United States Patent
Schmid et al.

(10) Patent No.: US 11,384,047 B2
(45) Date of Patent: Jul. 12, 2022

(54) METHOD FOR PREPARATION OF DECOLORIZED ACETOACETYLATED GLYCEROL WITH ACTIVATED CARBON

(71) Applicant: ARXADA AG, Visp (CH)

(72) Inventors: Leo Schmid, Ried-Brig (CH); Anja Bierstedt, Visp (CH)

(73) Assignee: ARXADA AG, Visp (CH)

( * ) Notice: Subject to any disclaimer, the term of this patent is extended or adjusted under 35 U.S.C. 154(b) by 0 days.

(21) Appl. No.: 17/434,435

(22) PCT Filed: Apr. 6, 2020

(86) PCT No.: PCT/EP2020/059727
§ 371 (c)(1),
(2) Date: Aug. 27, 2021

(87) PCT Pub. No.: WO2020/207952
PCT Pub. Date: Oct. 15, 2020

(65) Prior Publication Data
US 2022/0089519 A1  Mar. 24, 2022

(30) Foreign Application Priority Data

Apr. 10, 2019 (EP) .................................. 19168306
May 3, 2019 (EP) .................................. 19172516

(51) Int. Cl.
*C07C 67/56* (2006.01)
*C07C 69/72* (2006.01)

(52) U.S. Cl.
CPC .............. *C07C 67/56* (2013.01); *C07C 69/72* (2013.01)

(58) Field of Classification Search
CPC .......... C07C 67/56; C07C 67/48; C07C 69/72
See application file for complete search history.

(56) References Cited

U.S. PATENT DOCUMENTS

| | | | |
|---|---|---|---|
| 5,093,044 A | 3/1992 | Wretlind et al. | |
| 5,128,107 A * | 7/1992 | Katoh | B01D 3/32 210/411 |
| 5,693,850 A * | 12/1997 | Birkhahn | A61K 31/22 560/189 |
| 6,706,414 B1 | 3/2004 | Dammann et al. | |

FOREIGN PATENT DOCUMENTS

WO    WO9002549    3/1990

OTHER PUBLICATIONS

Toshiaki Nishihata et al., Aduvant effects of gyceryl esters of acetoacetic acid on rectal absorption of insulin and inulin in rabbits, Journal of Pharmaceutical Sciences, vol. 2, No. 3, pp. 280-285 (Year: 1983).*
International Search Report and Written Opinion for PCT/EP2020/059727 dated Jun. 11, 2020, 14 pages.
Toshiaki Nishihata et al: "Adjuvant effects of glyceryl esters of acetoacetic acid on rectal absorption of insulin and inulin in rabbits", Journal of Pharmaceutical Sciences, vol. 72, No. 3, Mar. 1, 1983, pp. 280-285.

* cited by examiner

*Primary Examiner* — Yate' K Cutliff
(74) *Attorney, Agent, or Firm* — Dority & Manning, P.A.

(57) ABSTRACT

The invention discloses the use of activated carbon with a mesh size smaller than 80 for the decolorization of acetoacetylated glycerol.

5 Claims, No Drawings

METHOD FOR PREPARATION OF DECOLORIZED ACETOACETYLATED GLYCEROL WITH ACTIVATED CARBON

CROSS REFERENCE TO RELATED APPLICATIONS

This application is the U.S. National Stage entry of International Application Number PCT/EP2020/059727 filed under the Patent Cooperation Treaty having a filing date of Apr. 6, 2020, which claims priority to European Patent Application No. 19168306.9 having a filing date of Apr. 10, 2019, and European Patent Application No. 19172516.7 having a filing date of May 3, 2019 which are incorporated herein by reference.

The invention discloses the use of activated carbon with a mesh size smaller than 80 for the decolorization of acetoacetylated glycerol.

BACKGROUND OF THE INVENTION

Acetoacetylated glycerol is used as intermediate for the preparation of resins as disclosed in WO 2004/029118 A2

When acetoacetylated glycerol is prepared it may show a distinct yellow which is transferred to products prepared with such colorized acetoacetylated glycerol.

There was a need for a method for preparation of decolorized acetoacetylated glycerol.

Surprisingly it was found that activated carbon in granular form does not perform, whereas activated carbon in powder form performs well.

Abbreviations and Definitions

AA acetoacetylated or acetoacetyl
DABCO 1,4-Diazabicyclo[2.2.2]octane, CAS 280-57-9
eq equivalent, molar equivalent if not stated otherwise
mesh size the mesh size is determined according to USA STANDARD SIEVES ASTM SPECIFICATION E-11, ASTM E11:01

SUMMARY OF THE INVENTION

Subject of the invention is the use of activated carbon for the decolorization of acetoacetylated glycerol, wherein the activated carbon has a mesh size of smaller than 80.

DETAILED DESCRIPTION OF THE INVENTION

The decolorization may be done by contacting the acetoacetylated glycerol with activated carbon.

The contacting may be done by passing the acetoacetylated glycerol through activated carbon, or by suspending the activated carbon in the acetoacetylated glycerol and subsequent removal of the activated carbon from the acetoacetylated glycerol, for example by filtration.

The passing of the acetoacetylated glycerol through activated carbon can for example be done by filtering the acetoacetylated glycerol through activated carbon.

The acetoacetylated glycerol before the decolorization with activated carbon, such as before the contacting of the acetoacetylated glycerol with activated carbon, has a color, the color may be a yellow color.

The amount of activated carbon used for decolorization of the acetoacetylated glycerol is from 1 to 30 wt %, preferably from 2 to 20 wt %, more preferably from 3 to 15 wt %, even more preferably from 3 to 12.5 wt %, especially from 3 to 10 wt %, the wt % being based on the weight of acetoacetylated glycerol.

The time of contacting the acetoacetylated glycerol with the activated carbon can be from 10 sec to 12 h, preferably from 20 sec to 8 h, more preferably from 30 sec to 4 h, even more preferably from 1 min to 4 h, especially from 1 min to 2 h, more especially from 1 min to 1 h.

The contacting of the acetoacetylated glycerol with the activated carbon can be done at various temperature, preferably it is done at a temperature below the boiling point of acetoacetylated glycerol, such as at a temperature from 0 to 100° C., preferably from 10 to 75° C., more preferably from 10 to 50° C.

The contacting can be done under atmospheric pressure or under pressure above or below atmospheric pressure, for example when the contacting is done by a passing of the acetoacetylated glycerol through the activated carbon, such as by a filtration of the acetoacetylated glycerol through activated carbon, then pressure may be conveniently applied in order to accelerate said passing.

In one embodiment, the acetoacetylated glycerol has been prepared by a reaction of glycerol with diketene, preferably in the presence of a catalyst, the catalyst being preferably an amine catalyst, more preferably the catalyst is 4-dimethylaminopyridine or DABCO.

When a catalyst is used in the reaction of glycerol with diketene, then preferably the catalyst is present in the reaction in an amount of from 0.0001 to 0.001 eq, more preferably of from 0.0001 to 0.0005 eq, the eq being based on the molar amount of glycerol.

The acetoacetylated glycerol can be a mono- di- or triacetoacetylated glycerol or a mixture thereof, preferably it is a di- or triacetoacetylated glycerol or a mixture thereof.

In one embodiment, the average number of acetoacetyl groups per molecule of AA-glycerol in the AA-glycerol can be 1 to 3, preferably 2 to 3.

Further subject of the invention is a method for decolorization of acetoacetylated glycerol, wherein the acetoacetylated glycerol is contacted with activated carbon having a mesh size of smaller than 80.

EXAMPLES

Materials
Norit® Activated Carbon, Cabot Norit Nederland B.V., Amersfoort 3824 MJ, The Netherlands
CEKA CPL Activated Carbon, Acticarbone® CPL, former product of CECA, a Subsidiary of Arkema Group, now Calgon Carbon Corporation, Moon Township, Pa. 15108, USA

Example 1: Screening of Activated Carbon Types for Decolorization of AA-Glycerol General Procedure AA-Glycerol (50 ml, prepared according to Example 3 and having distinct yellow color) was charged into a 100 ml glass bottle and heated to 40° C. under stirring. Then, activated carbon (2.5 g) was added to the AA-Glycerol and was suspended in the liquid by stirring for ca. 1 min. Then the stirrer was switched off and after 10 min the mixture was filtered through a glass frit filter. The decolorization performance was measured visually.

Examples 1a to 1d were done with different types of activated carbon, details are given in Table 1.

TABLE 1

| | Substrate | Form | Color |
|---|---|---|---|
| | AA-Glycerol, untreated before treatment with activated carbon | liquid | distinct yellow |

| Example | Activated Carbon Type | Form | Visual Decolorization Performance on AA-Glycerol |
|---|---|---|---|
| 1a | Norit ® GAC 1240 W | granular[a] | remained distinct yellow |
| 1b | Norit ® GAC 1240 PLUS | granular[a] | remained distinct yellow |
| 1c | Norit ® C GRAN | granular[a] | remained distinct yellow |
| 1d | Norit ® CA1 | powdered[b] | turned colorless |
| 1e | CECA CPL | powdered[b] | turned colorless |

[a] mesh size greater than 80
[b] mesh size smaller than 80

Example 2: Decolorization with Activated Carbon

The Norit® CA1 was suspended in AA-Glycerol (prepared according to Example 3 and having distinct yellow color) and was filtered onto a lab-scale Bokela pressure nutsche filter with 20 cm² filter area covered with a glass fiber pad. Then, 106.5 g of untreated AA-Glycerol where pressed through the pre-coat applying the conditions as given in Table 2:

TABLE 2

| Filter pad | 0.8 micro-meter glass fiber |
|---|---|
| Temperature | 40° C. |
| AA-Glycerol filtered | 106.5 g |
| Amount of activated carbon | 3.0 g |
| Filtration time | 762 s |
| Pressure | 2 bar |
| Cake thickness | 4 mm |

The filtrate was collected successively in 5 fractions of 20 ml and visually evaluated. Table 3 show the results of decolorization.

TABLE 3

| | Color |
|---|---|
| AA-Glycerol, untreated | distinct yellow |
| Fraction 1 | Clear, colorless |
| Fraction 2 | Clear, colorless |
| Fraction 3 | Clear, colorless |

Example 3: Synthesis of AA-Glycerol 500 g of glycerol (5.43 mol, 1 eq, >99%, Sigma-Aldrich) were added to a 2 L stirred glass reactor and heated to 40° C. As soon as the temperature was reached, 0.2 g of 4-dimethylaminopyridine were added as a catalyst (0.0016 mol, 0.0003 eq, >99%, Sigma-Aldrich). After 15 min, 1324 g of diketene (15.75 mol, 2.90 eq) were dosed to the reactor over 15 h with a constant dosing rate, keeping the temperature at 40° C. by cooling. After the diketene addition, the reactor content was kept at 40° C. for another 7 h. 1808 g of AA-glycerol were obtained having a distinct yellow color.
Density: 1.10 at 20° C.

The average number of acetoacetyl groups per molecule of AA-glycerol in the AA-glycerol was 2.5 to 3.

The invention claimed is:

1. A method for decolorizing acetoacetylated glycerol using activated carbon comprising, contacting the acetoacetylated glycerol with the activated carbon, wherein the activated carbon has a mesh size of smaller than 80.

2. The method according to claim 1, wherein the amount of activated carbon used for decolorizing the acetoacetylated glycerol is from 1 to 30 wt %, the wt % being based on the weight of acetoacetylated glycerol.

3. The method according to claim 1, wherein the time of contacting the acetoacetylated glycerol with the activated carbon is from 10 sec to 12 h.

4. The method according to claim 1, wherein the contacting of the acetoacetylated glycerol with the activated carbon is done at a temperature below the boiling point of acetoacetylated glycerol.

5. The method according to claim 1, wherein the acetoacetylated glycerol has been prepared by a reaction of glycerol with diketene.

* * * * *